United States Patent
Caponigro et al.

(10) Patent No.: US 9,474,754 B2
(45) Date of Patent: Oct. 25, 2016

(54) PHARMACEUTICAL COMBINATIONS COMPRISING A B-RAF INHIBITOR, AND EGFR INHIBITOR AND OPTIONALLY A PI3K-α INHIBITOR

(71) Applicants: Giordano Caponigro, Foxborough, MA (US); Darrin Stuart, Pleasant Hill, CA (US); Laure Moutouh-De Parseval, Basel (CH)

(72) Inventors: Giordano Caponigro, Foxborough, MA (US); Darrin Stuart, Pleasant Hill, CA (US); Laure Moutouh-De Parseval, Basel (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/419,256

(22) PCT Filed: Aug. 5, 2013

(86) PCT No.: PCT/US2013/053619
§ 371 (c)(1),
(2) Date: Feb. 3, 2015

(87) PCT Pub. No.: WO2014/025688
PCT Pub. Date: Feb. 13, 2014

(65) Prior Publication Data
US 2015/0265616 A1    Sep. 24, 2015

Related U.S. Application Data

(60) Provisional application No. 61/680,473, filed on Aug. 7, 2012.

(51) Int. Cl.
*A61K 39/00* (2006.01)
*A61K 31/506* (2006.01)
*A61K 31/4439* (2006.01)
*A61K 31/517* (2006.01)
*A61K 39/395* (2006.01)

(52) U.S. Cl.
CPC ......... *A61K 31/506* (2013.01); *A61K 31/4439* (2013.01); *A61K 31/517* (2013.01); *A61K 39/39558* (2013.01)

(58) Field of Classification Search
None
See application file for complete search history.

(56) References Cited

U.S. PATENT DOCUMENTS

2012/0045433 A1    2/2012    Dhingra et al.

FOREIGN PATENT DOCUMENTS

| WO | 2008/124161 A1 | 10/2008 |
|----|----------------|---------|
| WO | 2010/029082    | 3/2010  |
| WO | 2011/025927    | 3/2011  |
| WO | 2011/028540    | 3/2011  |
| WO | 2011/046894    | 4/2011  |
| WO | 2012062694     | * 5/2012 |
| WO | 2013/070998    | 5/2013  |

OTHER PUBLICATIONS

Caponigro et al. (Apr. 15, 2013) "Abstract 2337: Efficacy of the RAF/PI3Kα/anti-EGFR triple combination LGX818 + BYL719 + cetuximab in BRAFV600E colorectal tumor models," Cancer Res. vol. 73. Abstract 2337. In the Proceedings of the AACR 104th Annual Meeting 2013. Washington, DC.—Presentation abstract only.

International Preliminary Report on Patentability corresponding to International Patent Application No. PCT/US2013/053619, issued Feb. 10, 2015.

International Search Report corresponding to International Patent Application No. PCT/US2013/053619, mailed Sep. 18, 2013.

* cited by examiner

*Primary Examiner* — Sheela J Huff
(74) *Attorney, Agent, or Firm* — Brian C. Trinque; Lathrop & Gage LLP

(57) ABSTRACT

A pharmaceutical combination comprising (a) a B-Raf inhibitor, (b) a EGFR inhibitor and, optionally, (c) a PI3K inhibitor; the uses of such combination in the treatment of proliferative diseases; and methods of treating a subject suffering from a proliferative disease comprising administering a therapeutically effective amount of such combination.

16 Claims, No Drawings

PHARMACEUTICAL COMBINATIONS COMPRISING A B-RAF INHIBITOR, AND EGFR INHIBITOR AND OPTIONALLY A PI3K-α INHIBITOR

FIELD OF THE INVENTION

A combination of a B-Raf kinase inhibitor and an epidermal growth factor receptor (EGFR also known as ErbB-1 or HER-1) inhibitor and, optionally, a phosphatidylinositol 3-kinase (PI 3-kinases or PI3K) inhibitor which is used for the treatment of proliferative diseases. This invention also relates to the uses of such a combination in the treatment of proliferative diseases; to pharmaceutical compositions of the combination of agents and methods of treating a subject suffering from a proliferative disease comprising administering a therapeutically effective amount of such a combination to the subject.

BACKGROUND OF THE INVENTION

The protein kinases represent a large family of proteins, which play a central role in the regulation of a wide variety of cellular processes and maintaining control over cellular function. Aberrant kinase activity has been observed in many disease states including benign and malignant proliferative disorders as well as diseases resulting from inappropriate activation of the immune and nervous systems.

The Raf family of serine/threonine kinases include three members: C-Raf (or Raf-1), B-Raf and A-Raf. Activating alleles of B-Raf have been identified in ~70% of melanomas, 40% of papillary thyroid carcinoma, 30% of ovarian low-grade carcinoma, and 10% of colorectal cancers. Most B-Raf mutations are found within the kinase domain, with a single substitution (V600E) accounting for 80%. The mutated B-Raf proteins activate Raf-MEK-ERK pathway either via elevated kinase activity toward MEK or via activating C-Raf. The B-Raf inhibitor in the present combination therapy inhibits cellular processes involving B-Raf kinase by blocking the signal cascade in these cancer cells and ultimately inducing stasis and/or death of the cells. B-Raf inhibitors useful in the present combinations are generally and specifically described in published PCT patent application WO2011/025927, which is hereby incorporated by reference.

There are three classes of PI3-Kinases (PI3K). The class I enzymes consist of heterodimers having a regulatory (p85) domain and a catalytic (p110) subunit, of which there are four isoforms: p110α, p110β, p110δ and p110γ. The α and β isoforms are ubiquitously expressed; α is linked upstream mainly to receptor tyrosine kinases, whereas β can mediate signals from both G-protein-coupled receptors and from receptor tyrosine kinases. The δ and γ isoforms are expressed primarily in lymphocytes and play important roles in the regulation of immune responses.

A gain of function in PI3K signaling is common in many types of human cancer and include inactivation of the PTEN tumor suppressor gene, amplification/overexpression or activating mutations of some receptor tyrosine kinases (e.g. erbB3, erbB2, EGFR), amplification of genomic regions containing AKT, amplification of PIK3CA (the gene encoding p110α) and mutations in p110α. More than 30% of various solid tumor types were recently found to contain mutations of PIK3CA. From these mutation frequencies, PIK3CA is one of the most commonly mutated genes identified in human cancers. PI3K inhibitors useful in the present method, which have inhibitory activity for the α-isoform of PI3-kinases, are described in WO2010/029082 which is hereby incorporated by reference.

EGFRs are transmembrane receptors present on cell membranes. They have an extracellular binding component, a transmembrane component and an intracellular tyrosine kinase component. EGFRs play an important role in controlling normal cell growth, apoptosis and other cellular functions. Deregulation of EGFR activity can lead to continual or abnormal activation of the receptors causing unregulated cell division.

Epidermal growth factor receptor inhibitors are known in the art. Typically, they are either small molecule tyrosine kinase inhibitors, such as erlotinib and gefitinib, or monoclonal antibodies. Anti-EGFR monoclonal antibodies, such as cetuximab and panitumumab, are especially useful EGFR inhibitors for use in the present invention. Cetuximab, its preparation and use for treating proliferative diseases is disclosed in U.S. Pat. No. 6,217,866, which is here incorporated by reference. Panitumumab, its preparation and use for treating proliferative diseases is disclosed in U.S. Pat. No. 6,235,883, which is here incorporated by reference

SUMMARY OF THE INVENTION

The present invention relates to a therapeutic combination comprising: (a) a B-Raf inhibitor, (b) an EGFR inhibitor and, optionally, (c) a PI3K inhibitor, useful for separate, simultaneous or sequential administration to a subject in need thereof for treating or preventing a proliferative disease.

The present invention especially relates to a therapeutic combination comprising:
(a) a B-Raf inhibitor of the formula

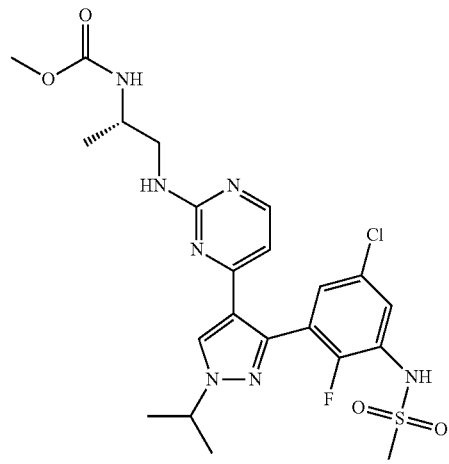 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof (hereinafter referred to as Compound A),
(b) an EGFR inhibitor, and, optionally,
(c) a PI3K inhibitor.

DETAILED DESCRIPTION OF THE INVENTION

The present invention relates to a therapeutic combination comprising: (a) a B-Raf inhibitor, (b) an EGFR inhibitor and, optionally, (c) a PI3K inhibitor, useful for separate, simultaneous or sequential administration to a subject in need thereof for treating or preventing a proliferative disease.

The present invention especially relates to a therapeutic combination comprising:
(a) a B-Raf inhibitor of the formula

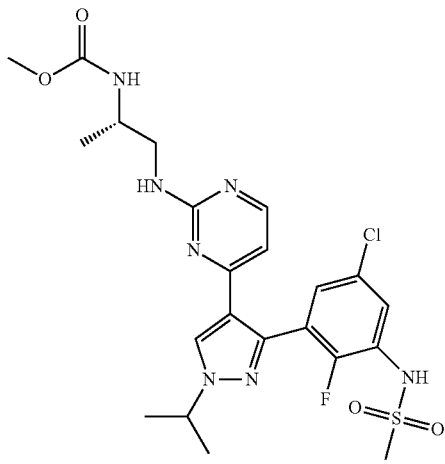 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof (hereinafter referred to as "Compound A"),
(b) an EGFR inhibitor, and, optionally,
(c) a PI3K inhibitor, especially a selective PI3Kα inhibitor.

The present invention especially relates to a therapeutic combination wherein the EGFR inhibitor is a tyrosine kinase inhibitor, such as erlotinib or gefitinib, especially erolitinib, and especially wherein the EGFR inhibitor is a monoclonal antibody, for example, cetuximab or panitumumab, especially cetuximab.

PI3K inhibitors are known in the art. The optional PI3K inhibitor is especially a selective PI3K-α inhibitor which is a 2-carboxamide cycloamino urea derivative described in WO2010/029082, particularly compounds of formula (I)

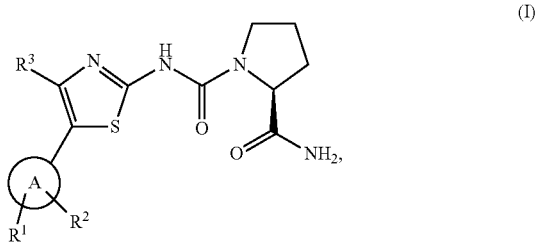

wherein
A represents a heteroaryl selected from the group consisting of:

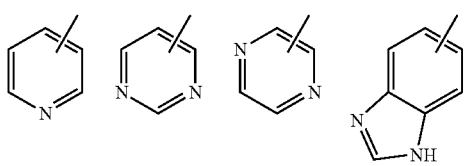

R1 represents one of the following substituents: (1) unsubstituted or substituted, preferably substituted C1-C7-alkyl, wherein said substituents are independently selected from one or more, preferably one to nine of the following moieties: deuterium, fluoro, or one to two of the following moieties C3-C5-cycloalkyl; (2) optionally substituted C3-C5-cycloalkyl wherein said substituents are independently selected from one or more, preferably one to four of the following moieties: deuterium, C1-C4-alkyl (preferably methyl), fluoro, cyano, aminocarbonyl; (3) optionally substituted phenyl wherein said substituents are independently selected from one or more, preferably one to two of the following moieties: deuterium, halo, cyano, C1-C7-alkyl, C1-C7-alkylamino, di(C1-C7-alkyl)amino, C1-C7-alkylaminocarbonyl, di(C1-C7-alkyl)aminocarbonyl, C1-C7-alkoxy; (4) optionally mono- or di-substituted amine; wherein said substituents are independently selected from the following moieties: deuterium, C1-C7-alkyl (which is unsubstituted or substituted by one or more substituents selected from the group of deuterium, fluoro, chloro, hydroxy), phenylsulfonyl (which is unsubstituted or substituted by one or more, preferably one, C1-C7-alkyl, C1-C7-alkoxy, di(C1-C7-alkyl)amino-C1-C7-alkoxy); (5) substituted sulfonyl; wherein said substituent is selected from the following moieties: C1-C7-alkyl (which is unsubstituted or substituted by one or more substituents selected from the group of deuterium, fluoro), pyrrolidino, (which is unsubstituted or substituted by one or more substituents selected from the group of deuterium, hydroxy, oxo; particularly one oxo); (6) fluoro, chloro;

R2 represents hydrogen;
R3 represents (1) hydrogen, (2) fluoro, chloro, (3) optionally substituted methyl, wherein said substituents are independently selected from one or more, preferably one to three of the following moieties: deuterium, fluoro, chloro, dimethylamino.

The radicals and symbols as used in the definition of a compound of formula I have the meanings as disclosed in WO2010/029082.

A preferred PI3K inhibitor is a compound which is specifically described in WO2010/029082. A very preferred selective PI3K-α inhibitor of the present invention is (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) or a pharmaceutically acceptable salt thereof, of the formula

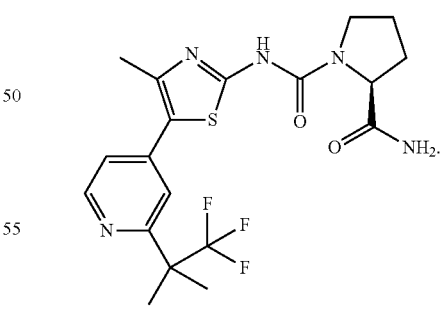

(herein referred to as "Compound B").

Hereinafter, dual combinations of Compound A and an EGFR inhibitor, triple combinations of Compound A, an EGFR inhibitor and a PI3K inhibitor of Formula I and more specifically dual combinations of Compound A and cetuximab and the triple combination of Compound A, cetuximab and Compound B will be referred to as a COMBINATION OF THE INVENTION.

The present invention particularly pertains to a COMBINATION OF THE INVENTION useful for separate, simultaneous or sequential administration to a subject in need thereof for treating or preventing a proliferative disease.

The present invention also pertains to a COMBINATION OF THE INVENTION for use in the preparation of a pharmaceutical composition or medicament for the treatment or prevention of a proliferative disease in a subject in need thereof.

The present invention further pertains to the use of a COMBINATION OF THE INVENTION for the preparation of a pharmaceutical composition or medicament for the treatment or prevention of a proliferative disease.

The present invention relates to a method of treating a subject having a proliferative disease comprising administering to said subject a COMBINATION OF THE INVENTION in a quantity which is jointly therapeutically effective against a proliferative disease.

The present invention further provides a commercial package comprising as therapeutic agents a COMBINATION OF THE INVENTION, together with instructions for simultaneous, separate or sequential administration thereof for use in the delay of progression or treatment of a proliferative disease.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination", "therapeutic combination" or "pharmaceutical combination", as used herein, defines either a fixed combination in one dosage unit form or a kit of parts for the combined administration where Compound A and Compound B may be administered independently at the same time or separately within time intervals that allow that the combination partners show a cooperative, e.g., synergistic, effect.

The term "pharmaceutical composition" is defined herein to refer to a mixture or solution containing at least one therapeutic agent to be administered to a subject, e.g., a mammal or human, in order to prevent or treat a particular disease or condition affecting the mammal.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

The term "a combined preparation" is defined herein to refer to especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g., in order to cope with the needs of a patient sub-population to be treated or the needs of the single patient.

The term "co-administration" or "combined administration" as used herein is defined to encompass the administration of the selected therapeutic agents to a single patient, and are intended to include treatment regimens in which the agents are not necessarily administered by the same route of administration or at the same time.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject.

The term "jointly therapeutically active" or "joint therapeutic effect" means that the therapeutic agents may be given separately (in a chronologically staggered manner, especially a sequence-specific manner) in such time intervals that they prefer, in the warm-blooded animal, especially human, to be treated, still show a (preferably synergistic) interaction (joint therapeutic effect). Whether this is the case can, inter alia, be determined by following the blood levels, showing that both compounds are present in the blood of the human to be treated at least during certain time intervals.

The term "pharmaceutically effective amount" or "clinically effective amount" or "therapeutically effective amount" of a combination of therapeutic agents is an amount sufficient to provide an observable improvement over the baseline clinically observable signs and symptoms of the disorder treated with the combination.

The term "subject" or "patient" as used herein includes animals, which are capable of suffering from or afflicted with a cancer or any disorder involving, directly or indirectly, a cancer. Examples of subjects include mammals, e.g., humans, dogs, cows, horses, pigs, sheep, goats, cats, mice, rabbits rats and transgenic non-human animals. In the preferred embodiment, the subject is a human, e.g., a human suffering from, at risk of suffering from, or potentially capable of suffering from cancers.

The term about" or "approximately" shall have the meaning of within 10%, more preferably within 5%, of a given value or range.

Compound A and/or Compound B may be administered in free form or in pharmaceutically acceptable salt form.

A "pharmaceutically acceptable salt", as used herein, unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts.

Unless otherwise specified, or clearly indicated by the text, or not applicable, reference to therapeutic agents useful in the COMBINATION OF THE INVENTION includes both the free base of the compounds, and all pharmaceutically acceptable salts of the compounds.

The present invention particularly pertains to a COMBINATION OF THE INVENTION useful for treating or preventing a proliferative disease in a subject in need thereof. In this embodiment of the present invention, the COMBINATION OF THE INVENTION is used for the treatment or prevention of a proliferative disease comprising administering to the subject a combination therapy, comprising an effective amount of Compound A and an effective amount an EGFR inhibitor, such as a monoclonal antibody EGFR inhibitor, especially, cetuximab or panitumumab, especially cetuximab. Preferably, these agents are administered at therapeutically effective dosages which, when combined, provide a beneficial effect. The administration may be separate, simultaneous or sequential.

The present invention further pertains to a COMBINATION OF THE INVENTION useful for treating or preventing a proliferative disease in a subject in need thereof. In this embodiment of the present invention, the COMBINATION OF THE INVENTION is used for the treatment or prevention of a proliferative disease comprising administering to the subject a triple combination therapy, comprising an effective amount of Compound A, an effective amount an EGFR inhibitor, such as a monoclonal antibody EGFR inhibitor, especially, cetuximab or panitumumab, especially cetuximab, and an effective amount of a selective PI3K-α inhibitor, especially a compound of Formula I, preferably Compound B. Preferably, these agents are administered at therapeutically effective dosages which, when combined, provide a beneficial effect. The administration may be separate, simultaneous and/or sequential.

Thus the present invention most particularly relates to a combination of
(a) a B-Raf inhibitor of the formula

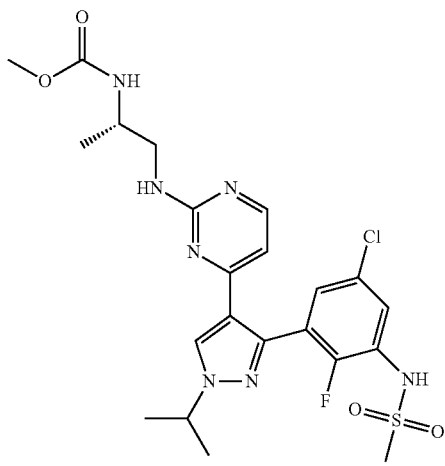 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof, and
(b) an EGFR inhibitor which is cetuximab.

Further, the present invention particularly relates to a triple combination of
(a) a B-Raf inhibitor of the formula

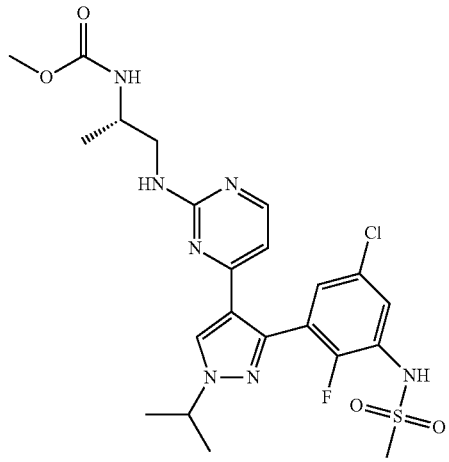 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof,
(b) an EGFR inhibitor which is cetuximab, and
(c) a PI3K inhibitor of the formula I, especially a PI3K inhibitor of the formula

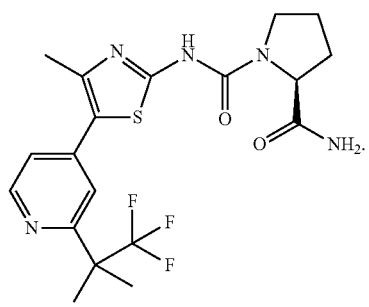 [SMILES: Cc1nc(NC(=O)N2CCC[C@H]2C(N)=O)sc1-c1ccnc(C(C)(C)C(F)(F)F)c1]

In one embodiment, the proliferative disease is cancer. The term "cancer" is used herein to mean a broad spectrum of tumors, including all solid tumors and hematological malignancies. Examples of such tumors include but are not limited to benign or malignant tumors of the brain, lung (in particular small-cell lung cancer and non-small cell lung cancer), squamous cell, bladder, gastric, pancreatic, breast, head and neck, renal, kidney, ureter, ovarian, prostate, colorectal, esophageal, testicular, gynecological (e.g., uterine sarcomas, carcinoma of the fallopian tubes, endometrial, cervix, vagina or vulva), thyroid, pancreatic, bone, skin, melanoma, uterine, ovarian, rectal, anal, colon, testicular, Hodgkin's disease, esophageal, small intestine, endocrine system (e.g., thyroid, parathyroid, or adrenal glands), sarcomas of soft tissues, urethra, penis, leukemia, lymphomas, neoplasms of the central nervous system, sarcomas, myeloma, biliary, liver, neurofibromatosis, acute myelogenous leukemia (AML), myelodysplastic syndromes (MDS), and Kaposi's sarcoma.

In a further embodiment of the present invention, the proliferative disease is melanoma, lung cancer (including non-small cell lung cancer (NSCLC), colorectal cancer (CRC), breast cancer, kidney cancer such as e.g., renal cell carcinoma (RCC), liver cancer, endometrial cancer, acute myelogenous leukemia (AML), myelodysplastic syndromes (MDS), thyroid cancer, particularly papillary thyroid cancer, pancreatic cancer, neurofibromatosis or hepatocellular carcinoma.

In a further embodiment of the present invention, the proliferative disease is a solid tumor. The term "solid tumor" especially means melanoma, breast cancer, ovarian cancer, colorectal cancer, and generally gastrointestinal tract, cervix cancer, lung cancer (including small-cell lung cancer and non-small cell lung cancer), head and neck cancer, bladder cancer, prostate cancer or Kaposi's sarcoma. The present combination inhibits the growth of solid tumors and also liquid tumors. Further, depending on the tumor type and particular combination used, a decrease of the tumor volume can be obtained. The COMBINATION OF THE INVENTION disclosed herein is also suited to prevent the metastatic spread of tumors and the growth or development of micrometastases. The COMBINATION OF THE INVENTION disclosed herein is suitable for the treatment of poor prognosis patients, especially such poor prognosis patients having metastatic melanoma, colorectal or pancreatic cancer.

In a further embodiment, the proliferative disease is melanoma or colorectal cancer, particularly colorectal cancer.

The COMBINATION OF THE INVENTION is particularly useful for the treatment of cancers having a genetic alteration in the RAS/RAF/MEK signal transduction pathway such as, for example, a B-Raf mutation or gene amplification.

In an important embodiment, the cancer to be treated is characterized by a B-Raf mutation, e.g., B-Raf mutated colorectal cancer. In particular, the B-Raf mutation is a V600 mutation, for example a V600E, V600K or V600G mutation.

Thus, the present invention particularly relates to a method of treating colorectal cancer characterized by a B-Raf mutation, which comprises administering a therapeutically effective amount of a COMBINATION OF THE INVENTION to a patient in need thereof.

More particularly, the present invention relates to a method of treating colorectal cancer characterized by a B-Raf mutation, which comprises administering a therapeutically effective amount of a combination of (a) a B-Raf inhibitor of the formula

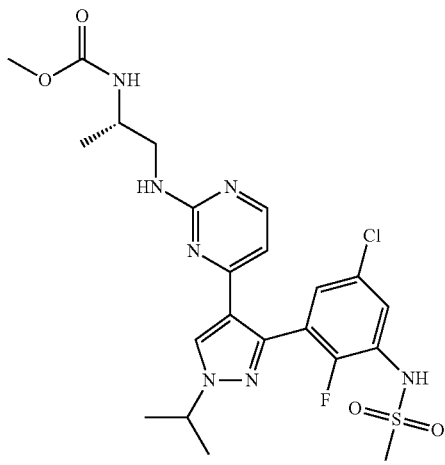 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof, and
(b) an EGFR inhibitor which is cetuximab.

Further, the present invention particularly relates to a method of treating colorectal cancer characterized by a B-Raf mutation, which comprises administering a therapeutically effective amount of a triple combination of (a) a B-Raf inhibitor of the formula

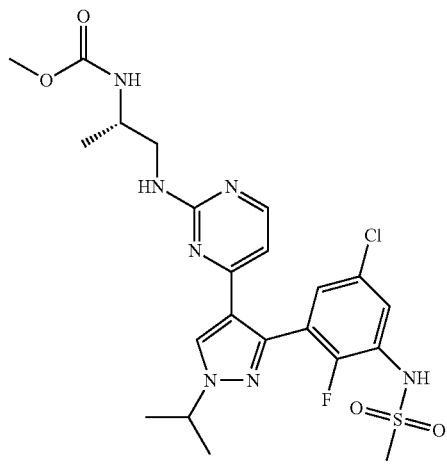 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof,
(b) an EGFR inhibitor which is cetuximab, and
(c) a PI3K inhibitor of the formula I, especially a PI3K inhibitor of the formula

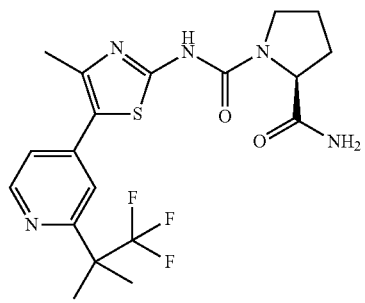 [SMILES: Cc1nc(NC(=O)N2CCC[C@H]2C(N)=O)sc1-c1ccnc(C(C)(C)C(F)(F)F)c1]

In an important embodiment of each of these methods, the B-Raf mutation is a V600 mutation, for example a V600E, V600K or V600G mutation.

The nature of proliferative diseases is multifactorial. Under certain circumstances, drugs with different mechanisms of action may be combined. However, just considering any combination of therapeutic agents having different mode of action does not necessarily lead to combinations with advantageous effects.

The administration of a pharmaceutical combination of the invention may result not only in a beneficial effect, e.g. a synergistic therapeutic effect, e.g. with regard to alleviating, delaying progression of or inhibiting the symptoms, but also in further surprising beneficial effects, e.g. fewer side-effects, more durable response, an improved quality of life or a decreased morbidity, compared with a monotherapy applying only one of the pharmaceutically therapeutic agents used in the combination of the invention.

A further benefit is that lower doses of the therapeutic agents of the COMBINATION OF THE INVENTION can be used, for example, that the dosages need not only often be smaller, but are also applied less frequently, or can be used in order to diminish the incidence of side-effects observed with one of the combination partners alone. This is in accordance with the desires and requirements of the patients to be treated.

It can be shown by established test models that a COMBINATION OF THE INVENTION results in the beneficial effects described herein before. The person skilled in the art is fully enabled to select a relevant test model to prove such beneficial effects. The pharmacological activity of a COMBINATION OF THE INVENTION may, for example, be demonstrated in a clinical study or in an animal model as essentially described hereinafter.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients may render impractical the use of this form of testing as a primary model for synergy. However, the observation of synergy in one species can be predictive of the effect in other species and animal models exist, as described herein, to measure a synergistic effect and the results of such studies can also be used to predict effective dose ratio ranges and the absolute doses and plasma concentrations required in other species by the application of pharmacokinetic/pharmacodynamic methods. Established correlations between tumor models and effects seen in man suggest that synergy in animals may be demonstrated, for example, by xenograft models or in appropriate cell lines.

Compound A is generally administered orally at a dose in the range from 10 mg to 1000 mg per day, for example 50 mg to 450 mg per day, or 100 mg to 400 mg per day. The daily dose can be administered on a qd or bid schedule.

The prescribing information for the ERBUTUX® brand of cetuximab instructs that it is initially administered at a dose of 400 mg/m$^2$ as a 120-minute intravenous infusion followed by weekly doses at 250 mg/m$^2$ infused over 60 minutes. Cetuximab is administered according to the prescribing information when used in the present combinations. However, dose reduction is also a possibility. Therefore, according to the present invention, cetuximab is administered initially at a dose of from 200 to 400 mg/m$^2$ followed by weekly doses of from 125 to 250 mg/m$^2$.

Compound B is generally administered orally in a dose in the range from 30 mg to 450 mg per day, for example 100 to 400 mg per day. The daily dose can be administered on a qd or bid schedule.

It is one objective of this invention to provide a pharmaceutical composition, comprising the COMBINATION OF THE INVENTION which is jointly therapeutically effective against a proliferative disease. In this composition, the combination partners Compound A and/or Compound B can be administered in a single formulation or unit dosage form, administered concurrently but separately, or administered sequentially by any suitable route. Preferably, the oral dosage forms of Compound A and Compound B are administered concurrently but separately.

The monoclonal antibody EGFR inhibitor is typically separately administered as intravenous infusion, preferably on a once weekly schedule when the EGFR inhibitor is cetuximab.

In one embodiment, the present invention also pertains to a COMBINATION OF THE INVENTION for use in the preparation of a pharmaceutical composition or medicament for the treatment or prevention of a proliferative disease in a subject in need thereof.

The individual combination partners of the COMBINATION OF THE INVENTION may be administered separately at different times during the course of therapy or concurrently in divided or single combination forms. The invention is therefore to be understood as embracing all such regimens of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, and the severity of the condition being treated. Thus, the dosage regimen of the COMBINATION OF THE INVENTION is selected in accordance with a variety of factors including the route of administration and the renal and hepatic function of the patient. A clinician or physician of ordinary skill can readily determine and prescribe the effective amount of the single therapeutic agents required to alleviate, counter or arrest the progress of the condition.

The optimum ratios, individual and combined dosages, and concentrations of the combination partners (a) and (b) of the COMBINATION OF THE INVENTION that yield efficacy without toxicity are based on the kinetics of the therapeutic agents' availability to target sites, and are determined using methods known to those of skill in the art.

The effective dosage of each of the combination partners may require more frequent administration of one of the compound(s) as compared to the other compound(s) in the combination. Therefore, to permit appropriate dosing, packaged pharmaceutical products may contain one or more dosage forms that contain the combination of compounds, and one or more dosage forms that contain one of the combination of compounds, but not the other compound(s) of the combination.

When the combination partners, which are employed in the COMBINATION OF THE INVENTION, are applied in the form as marketed as single drugs, their dosage and mode of administration can be in accordance with the information provided on the package insert of the respective marketed drug, if not mentioned herein otherwise.

The optimal dosage of each combination partner for treatment of a proliferative disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages may be established using routine testing and procedures that are well known in the art.

The amount of each combination partner that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage may vary depending on the compound used and the particular condition to be treated or prevented. Patients may generally be monitored for therapeutic effectiveness using assays suitable for the condition being treated or prevented, which will be familiar to those of ordinary skill in the art.

The present invention relates to a method of treating a subject having a proliferative disease comprising administering to said subject a COMBINATION OF THE INVENTION in a quantity, which is jointly therapeutically effective against a proliferative disease. In particular, the proliferative disease to be treated with a COMBINATION OF THE INVENTION is colorectal cancer, particularly a B-Raf mutated colorectal cancer, for example, a V600 B-Raf mutated colorectal cancer. Furthermore, the treatment can comprise surgery or radiotherapy.

The present invention further relates to the COMBINATION OF THE INVENTION for use in the treatment of a proliferative disease, particularly cancer, in particular B-Raf mutated colorectal cancer, such as a V600 B-Raf mutated colorectal cancer.

The present invention further provides a commercial package comprising as therapeutic agents a COMBINATION OF THE INVENTION, together with instructions for simultaneous, separate or sequential administration thereof for use in the delay of progression or treatment of a proliferative disease in a subject in need thereof.

The following Examples illustrate the invention described above; they are not, however, intended to limit the scope of the invention in any way. The beneficial effects of the pharmaceutical combination of the present invention can also be determined by other test models known as such to the person skilled in the pertinent art.

Example 1

This is a multicenter, open-label, phase Ib dose escalation and randomized phase II study which will enroll approximately 124 patients with B-Raf mutant metastatic colorectal cancer (mCRC).

The aim of phase Ib (n~24) is to determine the maximum tolerated dose (MTD) and/or recommended phase two dose (RP2D) of Compound A in combination with cetuximab (dual combination) and the MTD and/or RP2D of Compound A in combination with Compound B and cetuximab (triple combination). In the first stage of dose escalation, cohorts of patients will be treated with the dual combination until the MTD/RP2D of the dual combination is identified. Then, cohorts of patients will be treated with the triple combination during the second stage of dose escalation until the MTD/RP2D of the triple combination is identified.

Phase II (n~100) will assess the clinical efficacy of the dual combination and the triple combination and will further characterize the safety of the drug combinations. Treatment will be administered in 28-day cycles until disease progression, unacceptable toxicity, withdrawal of informed consent, or death.

Tumor response will be evaluated locally by the investigator according to a guideline based on RECIST version 1.1. Each patient will be evaluated for all potential sites of tumor lesions at Screening/baseline and every 6 weeks after starting study treatment until disease progression. Screening/baseline imaging assessments may be performed within 21 days of treatment start. On-study tumor assessments have a ±7 day window, except for the first post-baseline tumor assessment. The first post-baseline tumor assessment should be performed 6 weeks (+7 day window permitted) after starting treatment. There will be a tumor assessment at the End of Treatment (±3 days) if the patient discontinues for any reason other than disease progression and the last tumor assessment has been performed >21 days prior to this day. Patients included in the phase II part of the study, who discontinue study treatment due to a reason other than disease progression, should be followed up monthly via a phone call and undergo tumor assessments every 6 weeks (±7 days) until disease progression or initiation of subsequent anti-neoplastic therapy, or death, whichever occurs first.

Molecular Pre-Screening

To enter the screening phase of the study, patients must have written documentation of KRAS wild-type status and BRAF V600 mutation, which should be obtained locally on a fresh tumor biopsy (preferred) or the most recent archival tumor sample available. The molecular pre-screening informed consent must be signed prior to any study-related molecular pre-screening procedure (not applicable if the mutational status was already assessed outside of the study).

Treatment Period

The treatment period will begin on Cycle 1 Day 1. During phase II, study treatment should be initiated ≤1 week following randomization. Study treatments will be administered during 28-day cycles and will continue until disease progression, unacceptable toxicity, withdrawal of informed consent, or death.

End of Treatment (EOT)

The EOT visit occurs within 14 days after the last administration of study treatment (Section 7.1.5). All participating patients must complete this visit even if they have had to discontinue prematurely.

Follow-Up Period

The follow-up period starts after the End of Treatment visit and continues until the completion of all follow-up assessments, including survival follow-up.

Population a) Patient Population

Both phases of the study, phase Ib and phase II, will be conducted in adult patients with metastatic colorectal cancer (mCRC) harboring wild-type KRAS and a BRAF V600 mutation, whose disease has progressed despite previous anti-neoplastic therapy or for whom no further effective standard therapy is available.

Patients enrolled in this study are not permitted to participate in parallel investigational drug or device studies. Additionally, patients who have completed the study must not be re-enrolled for a second course of treatment.

b) Inclusion Criteria

Patients eligible for inclusion in this study have to meet all of the following criteria:

1. Age ≥18 years at the start of dosing (phase Ib) or at the time of randomization (phase II)
2. Histological or cytological proof of metastatic colorectal cancer (mCRC)
3. Progression after at least one prior standard of care regimen or be intolerant to irinotecan-based regimens
4. Written documentation of KRAS wild-type and BRAF V600E mutation, or any other BRAF V600 mutation
5. Phase II only: fresh tumor biopsy at baseline
6. Evidence of measurable disease, as determined by RECIST v1.1.
   Note: Lesions in areas of prior radiotherapy or other locoregional therapies (e.g., percutaneous ablation) should not be considered measurable, unless lesion progression has been documented since the therapy.
7. Life expectancy ≥3 months
8. ECOG performance status ≤2

9. Negative serum pregnancy test within 72 hours prior to the first dose of study treatment in all women of child-bearing potential
10. Able to understand and voluntarily sign the informed consent form, and ability to comply with the study visit schedule and other protocol requirements. Written informed consent must be obtained prior to screen procedures.

c) Exclusion Criteria

Patients eligible for this study must not meet any of the following criteria:
1. Phase II only: previous treatment with cetuximab, panitumumab, and/or other EGFR inhibitors
2. Phase II only: previous treatment with RAF-inhibitors, PI3K-inhibitors, and/or MEK-inhibitors
3. Symptomatic or untreated leptomeningeal disease
4. Symptomatic brain metastasis. Patients previously treated or untreated for these conditions that are asymptomatic in the absence of corticosteroid therapy are allowed to enroll. Brain metastasis must be stable with verification by imaging (e.g. brain MRI or CT completed at screening demonstrating no current evidence of progressive brain metastases). Patients are not permitted to receive enzyme inducing anti-epileptic drugs.
5. Patients with diabetes mellitus requiring insulin treatment and/or with clinical signs or with fasting glucose ≥140 mg/dL/7.8 mmol/L, history of clinically significant gestational diabetes mellitus or documented steroid-induced diabetes mellitus
6. Known acute or chronic pancreatitis
7. Clinically significant cardiac disease including any of the following:
   Congestive heart failure requiring treatment (NYHA grade ≥2), LVEF <45% as determined by MUGA scan or ECHO, or uncontrolled hypertension (refer to WHO-ISH guidelines)
   History or presence of clinically significant ventricular arrhythmias or atrial fibrillation
   Clinically significant resting bradycardia
   Unstable angina pectoris ≤3 months prior to starting study drug
   Acute Myocardial Infarction (AMI) ≤3 months prior to starting study drug
   QTcF >480 msec
8. Patients with any of the following laboratory values at Screening/baseline:
   Absolute neutrophil count (ANC) <1,500/mm$^3$ [1.5×10$^9$/L]
   Platelets <100,000/mm$^3$ [100×10$^9$/L]
   Hemoglobin <9.0 g/dL
   Serum creatinine >1.5×ULN or calculated or directly measured CrCl<50% LLN (lower limit of normal)
   Serum total bilirubin >1.5×ULN
   AST/SGOT and/or ALT/SGPT >2.5×ULN, or >5×ULN if liver metastases are present
9. Impairment of gastrointestinal (GI) function or GI disease that may significantly alter the absorption of oral Compound A/Compound B (e.g., ulcerative diseases, uncontrolled nausea, vomiting, diarrhea, malabsorption syndrome, small bowel resection).
10. Previous or concurrent malignancy. Exceptions: adequately treated basal cell or squamous cell skin cancer; in situ carcinoma of the cervix, treated curatively and without evidence of recurrence for at least 3 years prior to study entry; or other solid tumor treated curatively, and without evidence of recurrence for at least 3 years prior to study entry.
11. Pregnant or nursing (lactating) women, where pregnancy is defined as the state of a female after conception and until the termination of gestation, confirmed by a positive hCG laboratory test (>5 mIU/mL).

Women of child-bearing potential, defined as all women physiologically capable of becoming pregnant, are not allowed to participate in this study UNLESS they are using highly effective methods of contraception throughout the study and for 3 months after study drug discontinuation.

Highly effective contraception methods include:
   Total abstinence
   Male or female sterilization
   Combination of any two of the following (a+b or a+c or b+c)
      a. Use of oral, injected, or implanted hormonal methods of contraception
      b. Placement of an intrauterine device (IUD) or intrauterine system (IUS)
      c. Barrier methods of contraception: condom or occlusive cap (diaphragm or cervical/vault caps) with spermicidal foam/gel/film/cream/vaginal suppository Post-menopausal women are allowed to participate in this study. Women are considered post-menopausal and not of child bearing potential if they have had 12 months of natural (spontaneous) amenorrhea with an appropriate clinical profile (e.g. age appropriate, history of vasomotor symptoms) or six months of spontaneous amenorrhea with serum Follicle-Stimulating Hormone (FSH) levels >40 mIU/mL or have had surgical bilateral oophorectomy (with or without hysterectomy) or tubal ligation at least six weeks prior to screening. In the case of oophorectomy alone, only when the reproductive status of the woman has been confirmed by follow-up hormone level assessment is she considered not of child bearing potential.

12. Sexually active males must use a condom during intercourse while taking the drug and for 3 months after stopping treatment and should not father a child in this period. A condom is required to be used also by vasectomized men in order to prevent delivery of the drug via seminal fluid.
13. History of thromboembolic or cerebrovascular events within the last 6 months, including transient ischemic attack, cerebrovascular accident, deep vein thrombosis, or pulmonary embolism.
14. Patients who have received radiation therapy (that includes >30% of the bone marrow reserve), chemotherapy, biological therapy (e.g., antibodies) within ≤4 weeks (6 weeks for nitrosourea, mitomycin-C), or who have been treated with continuous or intermittent small molecule therapeutics or investigational agents within 5 half-lives of the agent (or ≤4 weeks when half-life is unknown) prior to starting study drug or who have not recovered from the side effects of such therapy (except alopecia).
15. Patients who have undergone any major surgery within the last 2 weeks prior to starting study drug or who would not have fully recovered from previous surgery
16. Known human immunodeficiency virus (HIV) infection
17. Other severe, acute, or chronic medical or psychiatric condition or laboratory abnormality that may increase the risk associated with study participation or study drug administration or that may interfere with the interpretation of study results and, in the judgment of the investigator, would make the patient inappropriate for the study.

2) Treatment
  a) Study Treatment
The investigational drugs to be used in this study are Compound A and Compound B. The other drug to be used in this study is cetuximab.
The study treatments are:
  Dual combination: Compound A and cetuximab
  Triple combination: Compound A, Compound B, and cetuximab
  i) Dosing Regimens
Patients will be assigned (phase Ib) or randomized (phase II) to one of the following regimens.
  Dual combination: Compound A (QD or BID) and cetuximab (QW)
  Triple combination: Compound A (QD or BID), Compound B (QD or BID), and cetuximab (QW)
  Dose and Treatment Schedule

| Study treatments | Pharmaceutical form and route of administration | Dose | Frequency |
| --- | --- | --- | --- |
| Dual combination | | | |
| Compound A | capsule for oral use | as assigned | once or twice daily |
| cetuximab | intravenous infusion | 400 mg/m² initial infusion 250 mg/m² subsequent infusions | once weekly |
| Triple combination | | | |
| Compound A | capsule for oral use | as assigned | once or twice daily |
| Compound B | tablet for oral use | as assigned | once or twice daily |
| cetuximab | intravenous infusion | 400 mg/m² initial infusion 250 mg/m² subsequent infusions | once weekly |

Instructions for Administration of Compound A or Compound A+Compound B

Compound A and Compound B will be administered orally on a daily schedule (QD) as a flat-fixed dose, and not by body weight or body surface area. Should new evidence from ongoing studies indicate that twice daily (BID) regimen(s) may be preferred, a BID regimen of either Compound A and/or Compound B in combination with cetuximab may be explored by opening new cohorts in the phase Ib portion of the study. A single RP2D and schedule will be chosen for the phase II portion for each drug.

QD Dosing: Patients should be instructed to take Compound A capsules (and Compound B tablets, if applicable) daily with a large glass of water (~250 ml) in the morning approximately 1 hr after the completion of a light breakfast (e.g. non-grapefruit based juice, toast, and jam), at approximately the same time each day. Patients should continue to fast for 1 hr after administration. If the patient forgets to take the dose in the morning, then he/she should take the dose within 6 hrs after the missed dose. If more than 6 hours has passed, then the dose should be withheld that day and the patient should continue treatment with the next scheduled dose. If, for any reason, a breakfast was not consumed, then the patient should still take the scheduled morning dose with a glass of water. If this happens on days of full PK sampling, it should be documented in the eCRF.
  BID Dosing: The doses of Compound A (and Compound B, if applicable) should be taken 12±2 hours apart. Patients will be instructed to take doses daily with a large glass of water (~250 ml) in the morning approximately 1 hr after the completion of a light breakfast and in the evening approximately 1 hr after a light meal or snack, at approximately the same time each day. Patients should continue to fast for 1 hr after administration. If, for any reason, an evening meal was not consumed, then the patient should still take the scheduled evening dose with a glass of water. If only one of the two oral drugs (Compound A, Compound B) is administered by BID, both drugs should be taken together in the morning and only the BID administered drug should be taken in the evening.
  Doses should be taken at approximately the same time each day, except on the days when blood collection is scheduled at the clinic, at which time the patients should take their morning doses at the clinic.
  Compound A and Compound B will be dosed at the same time for patients that are assigned/randomized to the triple combination.
  On days when blood collection is scheduled at the clinic, patients will take oral study drugs in the clinic under the supervision of the investigator or designee. On all other days patients will take oral study drugs at home.
  Fasting Plasma Glucose Monitoring: On the days of fasting plasma glucose monitoring, patients must be fasting overnight for at least 8 hours prior to the blood collection. Fasting plasma glucose must be collected prior to administering any steroids if given on the same day for cetuximab premedication. A light breakfast may be consumed after fasting plasma glucose draw. Compound A (and Compound B, if applicable) may be administered 1 hour after breakfast. Patients should continue to fast for 1 hour after the administration of Compound A (and Compound B, if applicable).
  PK Sampling: On the days of PK sampling, patients must be fasting overnight for at least 8 hours prior to the light meal to achieve light fed conditions. Pre-dose PK samples should be collected just prior to intake of Compound A (and Compound B, if applicable).
  At each visit, responsible site personnel will ensure that the appropriate dose of each study drug is administered and will provide the patient with the correct amount of study drug(s) for subsequent dosing. Patients will be instructed to return unused study drugs to the site at each visit.
  Patients should be instructed to swallow the capsules/tablets whole and not to chew or crush them.

Any doses that are missed should be skipped and should not be replaced or made up during the next scheduled dosing or on a subsequent day, whichever applies.

Patients must avoid consumption of grapefruit, pomegranates, star fruits, Seville oranges or products containing the juice of each during the entire study and preferably 7 days before the first dose of study medications, due to potential CYP3A4 interaction with the study medications. Orange juice is allowed.

If vomiting occurs during the course of treatment, no re-dosing of the patient is allowed before the next scheduled dose. The occurrence and frequency of any vomiting and/or diarrhea (or increased stool frequency) must be noted in the AEs section of the eCRF. In addition, on the days of full PK sampling, the onset time of any episodes of vomiting within the first 4 hours post-dosing on that day must be noted in the corresponding Dose Administration Record PK eCRF.

The investigator or responsible site personnel should instruct the patient to take the study drugs as per protocol (promote compliance). All dosages prescribed and dispensed to the patient and all dose changes and all missed doses during the study must be recorded on the Dosage Administration Record eCRF. Drug accountability must be performed on a regular basis. Patients will be instructed to return unused study drugs to the site at the end of each cycle. The site personnel will ensure that the appropriate dose of each study drug is administered at each visit and will provide the patient with the correct amount of drugs for subsequent dosing.

Cetuximab Administration

Cetuximab will be administered intravenously weekly on Days 1, 8, 15 and 22 (±3 days) of every cycle at the study site according to institutional standards. Pre-medication should be administered as described following institutional standards 30 minutes prior to cetuximab infusion. The cetuximab initial administered dose (Cycle 1 Day 1) is 400 mg/m$^2$ as a 120-minute intravenous infusion followed by 250 mg/m$^2$ weekly dose infused over 60 minutes. The infusion rate should not exceed 10 mg/min. Close monitoring is required during the infusion and for at least 1 hr after the end of the infusion.

If an infusion reaction occurs while cetuximab is being administered, the infusion should be stopped immediately and the patients should be closely monitored and treated in line with institutional standards.

Sequence of Drug Administration

Pre-medication that has the potential to alter the pH of the upper gastro-intestinal (GI) tract may alter the solubility of Compound A and/or Compound B and hence its bioavailability. These agents include, but are not limited to proton-pump inhibitors (e.g., omeprazole), H2-antagonists (e.g., ranitidine) and antacids. Therefore, oral dosing of Compound A (and Compound B, if applicable) will be administered prior to cetuximab and its premedication, which should preferably be based on a combination of an H1-antagonist (e.g. diphenhydramine) and dexamethasone (10 mg IV). A minimum of 1 hour must pass from the time of Compound A (and Compound B, if applicable) administration to the administration of cetuximab premedication. Cetuximab infusion is recommended to occur 0.5 hrs post-premedication (i.e. 1.5 hrs post-Compound A/Compound B intake).

Treatment Duration

Patients may continue treatment with the study drug until experiencing unacceptable toxicity, disease progression and/or the treatment is discontinued at the discretion of the investigator or withdrawal of consent.

Dose Escalation Guidelines

Starting Dose Rationale (1) Dual Combination

The starting dose for the dual combination study drugs is 100 mg QD for Compound A, and 400 mg/m$^2$ initial dose (Cycle 1 Day 1) and 250 mg/m$^2$ subsequent weekly doses as an intravenous infusion for cetuximab. These starting doses are based on available data from the ongoing first in human study of Compound A and the recommended cetuximab dose for metastatic colorectal cancer, according to the cetuximab label. Taking into consideration all information currently available about the dose-DLT relationships of Compound A and cetuximab as single agents and the uncertainty about the toxicity of the combination, the prior distribution of DLT rates indicates that the proposed starting dose combination meets the escalation with overdose control (EWOC) criteria.

(2) Triple Combination

The starting doses of Compound A, Compound B, and cetuximab during the triple combination, are based on all available data for all three drugs. Compound A and cetuximab will be administered at 50% and 100% of the determined MTD/RP2D of the dual combination, respectively. The starting dose of Compound B is expected to be 100 mg QD, which is 25% of the single agent MTD identified during a phase I clinical study of Compound B administered to patients with solid tumors.

No DDI on the PK level is expected between Compound B and cetuximab. Since Compound A is an inhibitor of BCRP and Compound B is a substrate of BCRP, there is a potential for increased Compound B exposure when co-administered with Compound A. Given the favorable bioavailability observed pre-clinically (58% in rat ADME) and clinically, the maximum possible increase in Compound B exposure is expected to be less than 60%. Therefore, the starting dose of Compound B is set at 100 mg QD to provide sufficient safety margin. In addition, Compound B is a time dependent inhibitor of CYP3A4. Compound A is mainly metabolized by CYP3A4. In accordance with the Food and Drug Administration's (FDA) recommended mechanistic static model, a 100 mg QD dose of Compound B when administered concomitantly with Compound A may increase the Compound A plasma AUC by up to 3 fold. To mitigate the potential increase in Compound A exposure when Compound B is added, the initial dose of Compound A in the triple combination (Compound A, Compound B, cetuximab) will be lowered to 50% of its MTD/RP2D identified during the dual combination, as stated above. In addition, rapid assessment of PK via in-life PK analysis will be implemented in the triple combination dose escalation phase to monitor Day 1 and Day 8 PK of Compound A and Compound B to inform dose escalation decisions. In case a DDI effect is observed and suggests over-exposure of Compound A, a dose reduction of Compound A may be implemented.

Before the first patient is dosed with the triple combination, the Bayesian model will be updated with the most recent data from the dual combination dose escalation phase to confirm that the proposed starting doses for Compound A and Compound B are still appropriate (i.e. fulfills the EWOC criteria) when administered with the identified dose of cetuximab from the dual combination. If the proposed starting dose does not meet the criteria, a lower dose combination will be used that satisfies the EWOC criteria.

Provisional Dose Levels

The tables below describe the starting doses and the provisional dose levels of study treatments for the dual (Compound A, cetuximab) and triple (Compound A, Compound B, cetuximab) combinations that may be evaluated during this trial. The dose of cetuximab will not be escalated, but may be reduced. Additional dose levels not currently specified may be enrolled and additional patients may be enrolled at a dose level already tested if such changes are deemed necessary to provide optimal safety and tolerability, pharmacokinetic, and pharmacodynamic data.

If at any time during the phase Ib portion of the study, emerging data from other clinical trials with Compound A and/or Compound B indicate that a BID dosing regimen of Compound A and/or Compound B regimen should be preferred, cohorts assessing BID dosing regimen(s) may be explored in the phase Ib portion of the study. If the decision is made to switch to BID, then the initial total daily dose (to be administered as two divided doses for BID) will be a dose that has previously been found to be well tolerated as a single daily dose, is below the MTD, and allowed by the BLRM.

Dose levels beyond the MTDs/RP2Ds determined during previous single agent studies of Compound A and Compound B will not be evaluated in this study.

Provisional Dose Levels (Dual Combination)

| Dose level | Compound A QD | Cetuximab weekly |
|---|---|---|
| −1** | 50 mg | Reduced dose*** |
| 1 (starting dose)* | 100 mg | 400 mg/m² on cycle 1 day 1 and 250 mg/m² weekly |
| 2 | 150 mg | 400 mg/m² on cycle 1 day 1 and 250 mg/m² weekly |
| 3 | 200 mg | 400 mg/m² on cycle 1 day 1 and 250 mg/m² weekly |
| 4 | 300 mg | 400 mg/m² on cycle 1 day 1 and 250 mg/m² weekly |
| 5 | 400 mg | 400 mg/m² on cycle 1 day 1 and 250 mg/m² weekly |

*It is possible for additional and/or intermediate and higher dose levels to be added during the course of the study. Cohorts may be added at any dose level below the MTD/RP2D in order to better understand safety, PK or PD.
**Dose level −1 represents treatment doses for patients requiring a dose reduction from the starting dose level.
***320 mg/m² on Cycle 1 Day 1 and 200 mg/m² weekly; or 240 mg/m² on Cycle 1 Day 1 and 150 mg/m² weekly Provisional Dose Levels (Triple Combination)

| Dose level | Compound B QD | Compound A QD | Cetuximab weekly |
|---|---|---|---|
| −1** | 50 mg | 50% MTD/RP2D of dual combination | Reduced dose*** |
| 1 (starting dose)* | 100 mg | 50% MTD/RP2D of dual combination | MTD/RP2D of dual combination |
| 2a | 100 mg | MTD/RP2D of dual combination | MTD/RP2D of dual combination |
| 2b | 200 mg | 50% MTD/RP2D of dual combination | MTD/RP2D of dual combination |
| 3 | 200 mg | MTD/RP2D of dual combination | MTD/RP2D of dual combination |
| 4 | 300 mg | MTD/RP2D of dual combination | MTD/RP2D of dual combination |
| 5 | 400 mg | MTD/RP2D of dual combination | MTD/RP2D of dual combination |

*It is possible for additional and/or intermediate and higher dose levels to be added during the course of the study. Cohorts may be added at any dose level below the MTD/RP2D in order to better understand safety, PK or PD.
**Dose level −1 represents treatment doses for patients requiring a dose reduction from the starting dose level. A dose lower than the dose indicated may be explored.
***320 mg/m² on Cycle 1 Day 1 and 200 mg/m² weekly; or 240 mg/m² on Cycle 1 Day 1 and 150 mg/m² weekly Example 2

The effect of combining Compound A with either the PI3Kα-specific inhibitor Compound B, or the EGFR inhibitor erlotinib, on the proliferation of BRAF-mutant CRC-derived cell lines is examined Both combinations synergistically inhibited proliferation in the majority of cells tested with the Compound A/Compound B and Compound A/erlotinib pairings active in 7/8 and 6/9 cell lines, respectively. Combinations were active in cells harboring both mutant and wild type alleles of the PI3Kα gene. In all cell lines tested only Compound A displayed significant single agent activity, although cell lines with either activating mutations in PI3Kα or loss of PTEN were largely refractory to all three compounds. Lastly, synergy between Compound A and Compound B was maintained, but the overall strength of the anti-proliferative effect was increased, when the EGFR-inhibitory antibody cetuximab was added as a third agent. Collectively these data support the combination of Compound A with either inhibitors of EGFR or PI3Kα. Furthermore, these results suggest that additional benefit maybe gained through the simultaneous addition of all three inhibitor types.

| | | CpdA IC50 [nM] | CpdB IC50 [nM] | Erlotinib IC50 [nM] | CpdA + CpdB | | CpdA + Erlotinib | | CpdA + CpdB + 50 nM Cetiximab | |
|---|---|---|---|---|---|---|---|---|---|---|
| Cell line | | | | | Mean | SD | Mean | SD | Mean | SD |
| SW1417 | CRC | 235 | >2700 | >2700 | 2.89 | 0.06 | 4.55 | 0.07 | 3.90 | 0.05 |
| COLO 205 | CRC | 5 | >2700 | >2700 | 3.80 | 0.06 | 4.02 | 0.06 | 3.68 | 0.05 |

-continued

| | | CpdA IC50 | CpdB IC50 | Erlotinib IC50 | Synergy Scores | | | | | |
|---|---|---|---|---|---|---|---|---|---|---|
| | | | | | CpdA + CpdB | | CpdA + Erlotinib | | CpdA + CpdB + 50 nM Cetiximab | |
| Cell line | | [nM] | [nM] | [nM] | Mean | SD | Mean | SD | Mean | SD |
| LS411N | CRC | 18 | >2700 | >2700 | 2.76 | 0.07 | 2.00 | 0.07 | 3.78 | 0.07 |
| CL-34 | CRC | 30 | >2700 | >2700 | 4.48 | 0.01 | 4.92 | 0.10 | 3.11 | 0.06 |
| MDST8 | CRC | 319 | ND | >2700 | ND | ND | 1.40 | 0.14 | ND | ND |
| HT-29* | CRC | 49 | >2700 | >2700 | 4.31 | 0.06 | 3.99 | 0.06 | 3.85 | 0.06 |
| RKO* | CRC | 1965 | >2700 | >2700 | 5.24 | 0.19 | 0.83 | 0.05 | 4.54 | 0.05 |
| SNU-C5* | CRC | >2700 | >2700 | >2700 | 2.44 | 0.10 | 3.51 | 0.07 | 3.23 | 0.08 |
| OUMS-23# | CRC | >2700 | >2700 | >2700 | 0.64 | 0.06 | 0.77 | 0.09 | ND | ND |

Single agent and combinatorial effects on proliferation of inhibitors of RAF (Compound A), PI3Kα (Compound B) and EGFR (erlotinib, cetuximab) in nine BRAF mutant CRC-derived cell lines. All cell lines express the BRAFV600E protein, except MDST8 which expresses the BRAFV600K variant. Cells harboring known or putative activating mutations in the PI3Kα gene are marked with a (*) and cells with PTEN loss marked with a (#). Cell proliferation was measured in 72 hr cell titer Glo™ assays and all results shown are the result of at least triplicate measurements. Shown are single agent IC50 values for each compound and synergy score measurements for each combination (described in Lehar J, Krueger A S, Avery W, et al (2009). Synergistic drug combinations tend to improve therapeutically relevant selectivity. Nat Biotechnol 27, 659-666). Interactions were deemed synergistic when scores ≥2.0 where observed. For triple combination synergy measurements, synergy between Compound A and Compound B was measured in a standard dose matrix format in the presence of a fixed concentration of cetuximab (50 nM).

Example 3

Evaluation of therapeutic interactions among a B-RAF inhibitor (Compound A), PI3K-α inhibitor (Compound B), and cetuximab are evaluated in the subcutaneous HT-29 human colorectal adenocarcinoma xenograft model. The cells were reported to be heterozygous for V600E mutant B-RAF (1799T>A in BRAF), P449T mutant PI3K-α (1345C>A in PIK3CA), and a point mutation and insertion in APC; and to be homozygous for point mutations in SMAD4 and TP53. No additional likely oncogenic mutations were found in 59 other genes whose alterations are frequently associated with neoplasia.

Compound A was stored at room temperature and suspended at 2.0 mg/mL in 0.5% carboxymethyl cellulose (CMC) and 0.5% Tween® 80 in deionized water (Vehicle 1). A fresh suspension was prepared every two weeks and stored at room temperature.

Compound B was stored at 4° C. and suspended at 2.5 mg/mL in 0.5% methylcellulose in deionized water (Vehicle 2). A fresh suspension was prepared weekly and stored at 4° C.

Cetuximab (ERBITUX®, ImClone/Bristol Myers Squibb, 2 mg/mL, Lot #1000039SA) was aliquotted at the beginning of the study and stored at 4° C.; a fresh aliquot was used on each day of dosing.

Paclitaxel dosing solutions at 3 mg/mL were prepared fresh on each treatment day by diluting aliquots of an in-house prepared paclitaxel stock (30 mg/mL paclitaxel in 50% ethanol: 50% Cremophor® EL) ten-fold with 5% dextrose in water. Dosing solutions were freshly prepared for one group at a time.

Each agent was administered at a single dose level, individually and in dual and triple combinations, that were initiated on Day 1 (D1) in female nude mice with established subcutaneous tumors. Body weight (BW) and health were monitored, and tumor volume was measured twice weekly for the duration of the study Animals were euthanized on D29 at 4 and 24 h after final dosing with Compound A and tumors were harvested from three animals per group at each time point. Efficacy was determined from mean tumor volume changes between D1 and D29. Prism summarizes test results as not significant (ns) at P>0.05, significant (symbolized by "*") at 0.01<P≤0.05, very significant ("") at 0.001<P≤0.01, and extremely significant ("*") at P≤0.001. The results are reported in the table below.

| Grp | n | Agent | mg/kg | Route | Schedule | Mean Volume, mm³ | | | | Statistical Significance | | | | | Regressions | | Mean BW Nadir | Deaths | |
|---|---|---|---|---|---|---|---|---|---|---|---|---|---|---|---|---|---|---|---|
| | | | | | | Day 1 | Day 29 | Change | T/C or T/T₀ | vs G1 | vs G2 | vs G3 | vs G4 | vs G8 | PR | CR | | TR | NTR |
| 1 | 10 | Vehicle 1 | — | po | bid x 28 | 122 | 1065 | 943 | — | — | — | — | — | — | 0 | 0 | −0.6% Day 8 | 0 | 0 |
| | | Vehicle 2 | | po | qd x 28 | | | | | | | | | | | | | | |
| 2 | 10 | Cpd. A | 20 | po | bid x 28 | 122 | 1016 | 894 | 95% | ns | — | — | — | — | 0 | 0 | −0.1% Day 8 | 0 | 0 |
| 3 | 10 | Cpd. B | 25 | po | qd x 28 | 122 | 660 | 538 | 57% | ns | — | — | — | — | 0 | 0 | −2.5% Day 8 | 0 | 0 |
| 4 | 10 | Cetuximab | 20 | ip | biwk x 4 | 125 | 955 | 830 | 88% | ns | — | — | — | — | 0 | 0 | −1.2% Day 8 | 0 | 0 |
| 5 | 10 | Cpd. A | 20 | po | bid x 28 | 125 | 491 | 366 | 39% | ns | ns | ns | — | *** | 0 | 0 | −0.7% Day 4 | 0 | 0 |
| | | Cpd. B | 25 | po | qd x 28 | | | | | | | | | | | | | | |

-continued

| Grp | n | Treatment Regimen Agent | mg/kg | Route | Schedule | Mean Volume, mm³ Day 1 | Day 29 | Change | T/C or T/T₀ | Statistical Significance vs G1 | vs G2 | vs G3 | vs G4 | vs G8 | Regressions PR | CR | Mean BW Nadir | Deaths TR | NTR |
|---|---|---|---|---|---|---|---|---|---|---|---|---|---|---|---|---|---|---|---|
| 6 | 10 | Cpd. A Cetuximab | 20 20 | po ip | bid x 28 biwk x 4 | 125 | 239 | 114 | 12% | ** | ** | — | ** | ns | 0 | 0 | — | 0 | 0 |
| 7 | 10 | Cpd. B Cetuximab | 25 20 | po ip | qd x 28 biwk x 4 | 125 | 584 | 459 | 49% | ns | — | ns | ns | *** | 0 | 0 | −1.4% Day 4 | 0 | 0 |
| 8 | 10 | Cpd A Cpd. B Cetuximab | 20 25 20 | po po ip | bid x 28 qd x 28 biwk x 4 | 123 | 120 | −3 | −2% | *** | *** | ** | *** | — | 0 | 0 | — | 0 | 0 |
| 9 | 10 | Paclitaxel | 30 | iv | qod x 5 | 122 | 229 | 107 | 11% | ** | — | — | — | — | 0 | 0 | −10.1% Day 11 | 0 | 0 |

Treatment efficacy was determined on D29, the day on which dosing Compound A was completed. For the purpose of statistical analyses, ΔTV, the difference in tumor volume between D1 (the start of dosing) and the endpoint day, was determined for every animal. For each treatment group, the response on the endpoint day was calculated by one of the following relations:

$$T/C(\%) = 100 \times \Delta T / \Delta C, \text{ for } \Delta T > 0$$

$$T/T0(\%) = 100 \times \Delta T / T0, \text{ for } \Delta T < 0,$$

where
ΔT=(mean tumor volume of the treated group on the endpoint day)−(mean tumor volume of the treated group on D1),
ΔC=(mean tumor volume of the control group on the endpoint day)−(mean tumor volume of the control group on D1), and
T0=mean tumor volume of the treated group on D1.
The T/T0 values are negative represent net tumor reduction for a group. A T/C value of 40% or less suggests potential therapeutic activity.
Response to Combination Therapies (Groups 5-8)

In Group 5, Compound A in dual combination with Compound B resulted in a ΔT of 366 mm³, corresponding to 39% T/C, and non-significant median tumor growth inhibition. The combination improved non-significantly upon Compound A monotherapy in Group 2 and Compound B monotherapy in Group 3.

In Group 6, Compound A in dual combination with cetuximab resulted in a ΔT of 114 mm³, corresponding to 12% T/C, and significant inhibition (P<0.01). The combination improved significantly upon Compound A monotherapy in Group 2 and cetuximab monotherapy in Group 4 (P<0.01).

In Group 7, Compound B in dual combination with cetuximab resulted in a ΔT of 459 mm³, corresponding to 49% T/C, and non-significant inhibition. The combination improved non-significantly upon Compound B monotherapy in Group 3 and cetuximab monotherapy in Group 4.

Group 8, the triple combination of Compound A, Compound B, and cetuximab resulted in a ΔT of −3 mm³, corresponding to −2% T/T0, and significant activity (P<0.001). This treatment improved significantly upon Compound A monotherapy in Group 2 (P<0.001), Compound B monotherapy in Group 3 (P<0.01), and cetuximab monotherapy in Group 4 (P<0.001). In addition, it improved significantly upon dual combinations with Compound A/Compound B in Group 5 and Compound B/cetuximab in Group 7 (P<0.01), and non-significantly upon the Compound A/cetuximab dual combination in Group 6.

The invention claimed is:
1. A pharmaceutical combination comprising:
(a) a B-Raf inhibitor of the formula

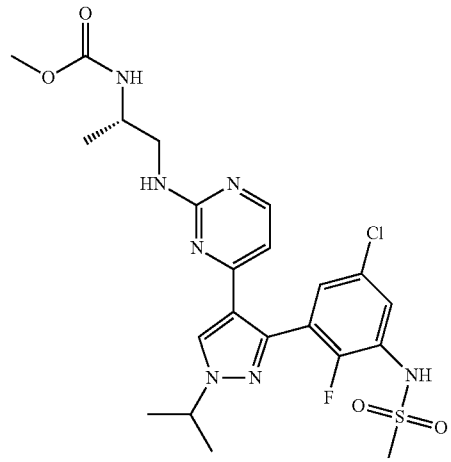 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof, and
(b) an EGFR inhibitor, wherein the EGFR inhibitor is erlotinib or cetuximab, and, optionally,
(c) a PI3K-α inhibitor, wherein the PI3K-α inhibitor is Compound B

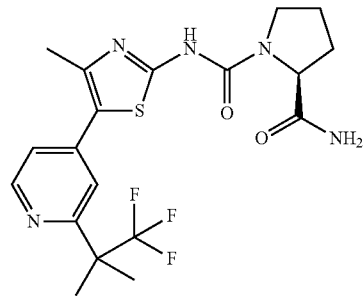 [SMILES: Cc1nc(NC(=O)N2CCC[C@H]2C(N)=O)sc1-c1ccnc(C(C)(C)C(F)(F)F)c1]

wherein the B-Raf inhibitor, the EGFR inhibitor, and Compound B are each formulated as single formulations for simultaneous, separate or sequential administration.

2. The pharmaceutical combination of claim 1 wherein the EGFR inhibitor is erlotinib.

3. The pharmaceutical combination of claim 1 wherein the EGFR inhibitor is cetuximab.

4. A method for treating a proliferative disease in a human patient wherein the proliferative disease is characterized by a B-Raf mutation, comprising the simultaneous, separate or sequential administration of a therapeutically effective amount of
(a) a B-Raf inhibitor of the formula

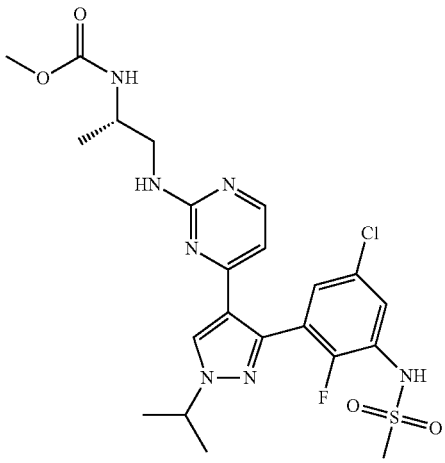 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof, and
(b) an EGFR inhibitor, wherein the EGFR inhibitor is erlotinib or cetuximab, and, optionally,
(c) a PI3K-α inhibitor, wherein the PI3K-α inhibitor is Compound B

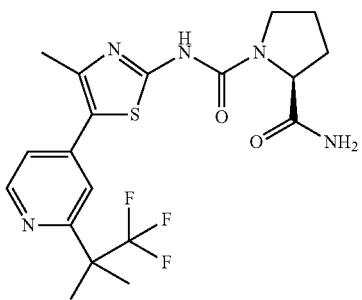 [SMILES: Cc1nc(NC(=O)N2CCC[C@H]2C(N)=O)sc1-c1ccnc(C(C)(C)C(F)(F)F)c1]

wherein the B-Raf inhibitor, the EGFR inhibitor, and Compound B are each formulated as single formulations.

5. The method according to claim 4 wherein the B-Raf mutation is a V600 mutation.

6. The method according to claim 4, wherein the proliferative disease is colorectal cancer.

7. The method according to claim 4, wherein the B-Raf inhibitor is administered orally in an amount of 10 mg per day to 1000 mg per day.

8. The method according to claim 4, wherein the B-Raf inhibitor is administered orally in an amount of 50 mg per day to 450 mg per day.

9. The method according to claim 7, wherein the B-Raf inhibitor is administered once or twice per day.

10. The method according to claim 4, wherein the EGFR inhibitor is cetuximab, wherein the cetuximab is administered as an intravenous infusion in an amount of 200 mg/m$^2$ to 400 mg/m$^2$ followed by weekly doses of from 125 mg/m$^2$ to 250 mg/m$^2$.

11. The method according to claim 4, wherein Compound B is administered orally in an amount of 30 mg per day to 450 mg per day.

12. The method according to claim 11, wherein Compound B is administered once or twice per day.

13. The method according to claim 4, wherein the B-Raf inhibitor and cetuximab are administered separately.

14. The method according to claim 4, wherein the B-Raf inhibitor and Compound B are administered simultaneously.

15. The method according to claim 5, wherein the V600 mutation is a V600E mutation or a V600K mutation.

16. The method according to claim 6, wherein the colorectal cancer is characterized by a V600E mutation or a V600K mutation.

* * * * *